United States Patent [19]

Helbig et al.

[11] Patent Number: 5,006,516

[45] Date of Patent: Apr. 9, 1991

[54] METHOD FOR THE PROPHYLAXIS OF CARDIAC INFARCTIONS AND THE PREVENTION OF REINFARCTIONS

[75] Inventors: Joachim Helbig, Tutzing; Hans G. Classen, Stuttgart, both of Fed. Rep. of Germany

[73] Assignee: Verla-Pharm Arzneimittelfabrik Apotheker H.J.V. Ehrlich GmbH & Co. KG., Tutzing, Fed. Rep. of Germany

[21] Appl. No.: 345,276

[22] Filed: May 1, 1989

[30] Foreign Application Priority Data

May 2, 1988 [DE] Fed. Rep. of Germany ....... 3814856

[51] Int. Cl.$^5$ ............................................. A61K 31/60
[52] U.S. Cl. ..................................... 514/163; 514/159
[58] Field of Search ................................ 514/159, 163

[56] References Cited

U.S. PATENT DOCUMENTS 4,664,915  5/1987  Simonian ............................ 514/163

OTHER PUBLICATIONS

Chem. Abst. 106-182557t (1987).

*Primary Examiner*—Stanley J. Friedman
*Assistant Examiner*—Kevin Weddington
*Attorney, Agent, or Firm*—Venable, Baetjer, Howard & Civiletti

[57] ABSTRACT

The invention relates to an agent for the prophylaxis of cardiac infarctions and for the prevention or reinfarctions, and is characterized by the fact that said agent comprises a combination of magnesium amino dicarboxylic acid halides, basic magnesium amino dicarboxylic acid salts, and magnesium halides, singly or in combination, on the one hand, and acetylsalicylic acid, on the other hand, as well as conventional pharmaceutical carriers, diluents, and/or adjuvants, as required.

4 Claims, No Drawings

METHOD FOR THE PROPHYLAXIS OF CARDIAC INFARCTIONS AND THE PREVENTION OF REINFARCTIONS

The invention relates to an agent for the prophylaxis of cardiac infarctions and the prevention of reinfarctions.

It is known in the prior art that magnesium (II) ions have a wide spectrum of cardiovascular effect, which is primarily based on their properties antagonistic to Ca (II). This effect is especially pronounced in magnesium amino dicarboxylic acid halides, such as magnesium-L-aspartate-hydrochloride and magnesium-L-glutamate hydrochloride, which display a high absorption ratio. In addition to protecting the heart cells by virtue of their calcium antagonism, these compounds also have a spasmolytic effect on the coronary arteries, as well as a stress-reducing effect It has been repeatedly postulated that magnesium compounds should also have an inhibitory effect on platelet aggregation on the basis of their calcium antagonism. However, clinical investigations reveal that magnesium compounds do not demonstrate such an effect.

Since magnesium compounds do not inhibit platelet aggregation, and since there is a considerable need for an agent to prevent infarctions and reinfarctions having the widest possible range of effect, in view of the increasing number of cardiac infarctions and reinfarctions, the technical object of the invention is then to develop an agent for the prophylaxis of infarctions and the prevention of reinfarctions that will combat all possible biochemical causes of cardiac infarction and reinfarction.

The object of the invention is achieved by the prophylactic agent according to the invention. The prophylactic agent comprises an effective amount of a combination of both a magnesium compound and acetylsalicylic acid. The magnesium compound may be selected from the group consisting of magnesium dicarboxylic acid halides, basic magnesium amino dicarboxylic acid salts, magnesium halides, and combinations thereof. In addition, the agent may contain conventional pharmaceutical carriers, diluting agents and/or adjuvants, as needed.

The agent according to the invention thus prophylactically combats all known biochemical causes of cardiac infarction and reinfarction. Surprisingly, however, it was discovered that the known poor compatibility of the stomach and intestines to acetylsalicylic acid could be eliminated by the systemic effects of magnesium. In addition, systemic incompatibility with acetylsalicylic acid, such as allergic hyperreactions manifested in constriction of the unstriated musculature, is inhibited by magnesium.

The preferred magnesium amino dicarboxylic acid halides employed in the present invention are magnesium-L-aspartate hydrochloride or magnesium-L-glutamatehydrochloride. Magnesium amino dicarboxylic acid halides, their production and their structure are described in detail in the prior art literature. For example, see DE-PS No. 22 28 101, DE-OS No. 32 38 118, "Angewandte Chemie" ("Applied Chemistry"), vol. 98, 1986, issue 11, pages 1014 to 1016, and DE-PS No. 18 09 119.

The preferred basic magnesium amino dicarboxylic acid salts employed in the present invention are basic magnesium monoaspartate or basic magnesium glutamate. Basic magnesium monoaspartate $(Mg(CO_2CH_2CHNH_2CO_2) \times 3H_2O)$ is a white powder that does not melt below 300° C.; it can be produced by dissolving 225 g magnesium-L-diaspartate $\times 4H_2O$ in 250 ml distilled water, and then slowly adding a potassium hydroxide solution (80 g KOH tablet 85% in 100 ml distilled water) in the form of drops until a pH value of 10.2–10.6 is reached. The clear solution is stirred for one hour. The volume of the solution is then reduced to between 250–275 ml at 40° C. in a water jet vacuum (approximately 14 torr) and is left standing at room temperature. The solution crystallizes after about four days. The crystals are removed in a water jet vacuum by means of a frit and then washed, first with a small quantity of distilled water and then with acetone. The crystals are then dried at about 80–90° C. until the acetone odor disappears.

The basic magnesium glutamate is produced in similar fashion.

The basic magnesium amino dicarboxylic acid salts are preferably used in the agent of the present invention when the patient's stomach, to which the agents are directed, is overly acidic.

The preferred magnesium halide is magnesium chloride. The weight ratio of the magnesium compound(s) to the acetylsalicylic acid, as effctively employed in the agents according to the invention, is from about 1:1 to about 15:1.

In a specifically preferred embodiment of the present invention, the agents are administered orally, for example in the form of formulas, capsules, tablets, granules, powders, effervescent tablets, and solutions. The individul doses (daily doses) of the magnesium compound(s) can be 20 to 240 mg, calculated as $Mg^{2+}$, and for the acetylsalicylic acid 20 to 1,000 mg.

The agents according to the invention can be produced in the conventional manner by mixing the components and formulating them in the form desired for administration, wherein conventional carriers, diluents, and/or adjuvants can be employed.

What is claimed is:

1. A method for the prophylaxis of cardiac infarctions and for the prevention of reinfarctions in a mammal, comprising administering to said mammal a pharmaceutical agent comprising a pharmaceutically effective amount of a mixture of a magnesium compound and acetylsalicylic acid as the active ingredient and a pharmaceutically acceptable carrier, said magnesium compound selected from the group consisting of magnesium amino dicarboxylic acid halides, basic magnesium amino dicarboxylic acid salts, magnesium halides, and combinations thereof.

2. The method of claim 1 wherein said pharmaceutical agent further comprises pharmaceutically acceptable diluents, adjuvants or mixtures thereof.

3. The method of claim 1 wherein the weight ratio of magnesium compound to salicylic acid in from about 1:1 to about 15:1.

4. The method of claim 2 wherein the weight ratio of magnesium compound to salicylic acid is from about 1:1 to about 15:1.

* * * * *